(12) United States Patent
Takeuchi et al.

(10) Patent No.: US 7,005,089 B2
(45) Date of Patent: Feb. 28, 2006

(54) FLAME RETARDANT TREATING AGENTS, FLAME RETARDANT TREATING PROCESS AND FLAME RETARDANT TREATED ARTICLES

(75) Inventors: Narihisa Takeuchi, Fukui (JP); Keiichiro Sada, Fukui (JP); Toru Makino, Fukui (JP); Koji Midori, Fukui (JP)

(73) Assignee: Nicca Chemical Co., Ltd., Fukui (JP)

( * ) Notice: Subject to any disclaimer, the term of this patent is extended or adjusted under 35 U.S.C. 154(b) by 306 days.

(21) Appl. No.: 10/225,243

(22) Filed: Aug. 22, 2002

(65) Prior Publication Data

US 2003/0193045 A1    Oct. 16, 2003

(30) Foreign Application Priority Data

Apr. 12, 2002   (JP) .............................. 2002-110995

(51) Int. Cl.
*C07D 105/04* (2006.01)
*A01N 9/36* (2006.01)
*B01J 1/16* (2006.01)
*C08K 5/523* (2006.01)
*B32B 9/00* (2006.01)

(52) U.S. Cl. .................. 252/608; 252/609; 8/115.61; 8/115.56; 428/264; 428/265; 428/272; 428/273; 428/276; 428/277; 524/101; 524/148; 524/151; 524/230; 524/311

(58) Field of Classification Search ............. 8/115.56, 8/115.61, 94.61, 115; 252/608, 609; 428/264–265, 428/272–273, 276–277; 524/101, 148, 151, 524/230, 311, 117; 427/393; 57/904
See application file for complete search history.

(56) References Cited

U.S. PATENT DOCUMENTS

| | | | |
|---|---|---|---|
| 3,702,878 A | * | 11/1972 | Saito et al. .................... 558/82 |
| 3,883,463 A | | 5/1975 | Jin et al. |
| 4,317,769 A | * | 3/1982 | Saito et al. .................. 524/117 |
| 4,794,037 A | * | 12/1988 | Hosoda et al. .............. 442/139 |
| 5,320,785 A | | 6/1994 | Dermeik |
| 5,326,805 A | | 7/1994 | Sicken et al. |
| 5,780,534 A | | 7/1998 | Kleiner et al. |
| 6,013,707 A | | 1/2000 | Kleiner et al. |
| 6,121,445 A | | 9/2000 | Suzuki et al. |
| 6,136,973 A | | 10/2000 | Suzuki et al. |
| 6,207,736 B1 | | 3/2001 | Nass et al. |
| 6,255,371 B1 | | 7/2001 | Schlosser et al. |
| 6,365,071 B1 | | 4/2002 | Jenewein et al. |
| 6,538,054 B1 | * | 3/2003 | Klatt et al. ................. 524/101 |

FOREIGN PATENT DOCUMENTS

| | | |
|---|---|---|
| DE | 2 252 258 | 5/1974 |
| DE | 24 47 727 | 4/1976 |
| DE | 197 34 437 | 2/1999 |
| DE | 197 37 727 | 7/1999 |
| EP | 584 567 | 3/1994 |
| EP | 699 708 | 3/1996 |
| JP | 50-17979 | 6/1975 |
| JP | 55-124792 | 9/1980 |
| JP | 56-9178 | 2/1981 |
| JP | 60-259674 | 12/1985 |
| WO | WO 97/39053 | 10/1997 |
| WO | WO 98/08898 | 3/1998 |
| WO | WO98/39306 | 9/1998 |
| WO | WO98/45364 | 10/1998 |

* cited by examiner

*Primary Examiner*—Yogendra N. Gupta
*Assistant Examiner*—Preeti Kumar
(74) *Attorney, Agent, or Firm*—Leydig, Voit & Mayer, Ltd.

(57) ABSTRACT

Flame retardant treating agents according to the invention comprise a phosphorus-based compound represented by the following formula (4):

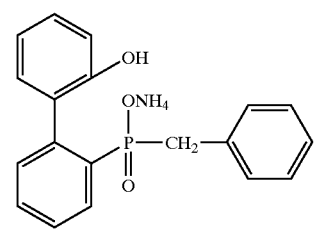

(4)

Flame retardant treated fibers can be obtained by immersion of polyester fiber woven fabrics and the like in a treatment solution containing the flame retardant treating agents and accomplishing heat treatment at a prescribed temperature. It is thereby possible to impart adequate flame retardance to polymer materials such as fibers and thermoplastic polymers even when used in small amounts, and provide flame retardant treating agents that contain no halogen compounds.

14 Claims, No Drawings

FLAME RETARDANT TREATING AGENTS, FLAME RETARDANT TREATING PROCESS AND FLAME RETARDANT TREATED ARTICLES

BACKGROUND OF THE INVENTION

1. Field of the Invention

The present invention relates to flame retardant treating agents, to a flame retardant treating process and to flame retardant treated articles composed of polymer materials such as fibers or thermoplastic polymers which have been flame retardant treated.

2. Related Background Art

Various treating agents and treating processes have been employed in the past to impart flame retardance by increasing the flameproof properties of combustible or flammable fibers or plastics.

There are commonly employed (a) halogenated cycloalkane compounds as flame retarding components in flame retardant treating agents used in flame retardant treating processes whereby fibers are imparted with a flame retardant property and given more prolonged cleaning durability (durability against wet washing such as water washing, or dry cleaning). Also, (b) Japanese Unexamined Patent Publication SHO No. 60-259674 discloses a flame retardant treating process employing as the flame retarding component a mixture of a halogenated cycloalkane compound such as hexabromocyclododecane with a phosphonate compound.

For plastics, and particularly thermoplastic polymers, (c) salts of phosphinic acid are known as effective flame retarding agents (see German Patent Application Publications No.2252258 and No.2447727). More specifically, in European Patent Application Publication No.699708 there are disclosed calcium phosphinate and aluminum phosphinate as flame retarding components which are particularly effective for polyesters, and it is stated that deterioration of the properties of polymer molded materials can be reduced in comparison to using alkali metal salts.

For several polymers, (d) synergistic combinations of phosphinic acid salts and certain nitrogen-containing compounds are described in the International Patent Application PCT/EP97/01664 pamphlet, in German Patent Application Publication No.19734437 and in German Patent Application Publication No.19737727, which disclose that the flame retardance is increased compared to using phosphinic acid salts alone. For example, one of the synergistic agents may be melamine or a melamine compound (for example, melamine cyanurate or melamine phosphate), and although these by themselves can impart a certain level of flame retardance to some thermoplastic materials, their combination with phosphinic acid salts can exhibit an even more notable effect.

SUMMARY OF THE INVENTION

Still, further improvement in performance is desired because these conventional flame retardant treating agents and flame retardant treating processes do not always impart sufficient flame retardance to the treated polymer materials such as fibers or plastics (treated articles). In particular, even using the synergistic combinations mentioned as (d) above for specific plastics is associated with problems, such as failure to achieve the V-0 rating of the internationally accepted UL94 standard, or a need for addition of large amounts of the flame retardant treating agent in order to obtain adequate flame retardance (flameproofness).

The publications mentioned for (d) above disclose higher molecular melamine derivatives as flame retardant agents. Examples of such melamine derivatives include the condensation products melam, melem and melon, as well as reaction products of these compounds with phosphoric acid (for example, melamine pyrophosphate and melamine polyphosphate). To the knowledge of the present inventors, however, it is necessary to use large amounts of these flame retardant agents for thermoplastic materials, particularly those reinforced with glass fiber.

On the other hand, with increasing awareness of issues such as protection of the natural environment and protection of living environments in recent years, there has been a demand for flame retardant treating agents which employ halogen-free compounds which contain no halogen elements. A flame retardant treating process which allows cleaning durability to be maintained even by post-treatment of fibers has also been strongly desired.

The present invention has been accomplished in light of these circumstances, and its object is to provide flame retardant treating agents, and a flame retardant treating process employing them, which can impart a sufficient flame retardant property to polymer materials such as fibers and thermoplastic polymers, even when used in small amounts, and which while containing no halogen compounds allow fibers to maintain adequate cleaning durability, as well as flame retardant treated articles that have been flame retardant-treated therewith.

As a result of much diligent research with the aim of achieving this object, the present inventors have completed the present invention upon finding that it is possible to solve the aforementioned problems by using specific phosphorus-based compounds as flame retarding components.

Specifically, a flame retardant treating agent according to the invention comprises a phosphorus-based compound represented by the following formula (1) and/or its salt:

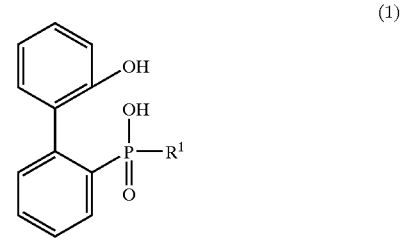

(1)

wherein $R^1$ represents an alkyl, hydroxyalkyl or substituted or unsubstituted aralkyl group, or a group represented by the following formula (2):

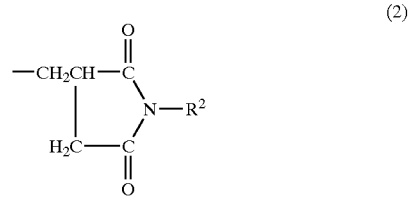

(2)

wherein $R^2$ represents an alkyl group of 1–10 carbons.

When used for flame retardant treatment by post-treatment of a polymer material such as fiber or a thermoplastic polymer which is to be treated, the flame retardant treating agent is attached onto the surface thereof or a portion thereof is incorporated into the molecular structure and fixed to it. A flame retardant treating agent comprising the phosphorus-based compound represented by formula (1) above or its salt will tend to infiltrate the amorphous regions of the molecules of the article on which it is treated, and when it is heated, the dense molecular configuration is relaxed, promoting its attachment and diffusion into the amorphous regions. As a result, the coverage of the flame retardant treating agent is increased, and fixing onto the treated article is reinforced. This effect is particularly notable when the treated article is fiber.

When, for flame retardant treatment of a plastic material such as a thermoplastic polymer, for example, the flame retardant treatment is carried out with a polymer blend by mixture of the thermoplastic polymer and the flame retardant treating agent or in cases where the flame retardant treating agent itself can be supplied as a polymer, sufficient flame retardance can be achieved using a smaller amount than with phosphinic acid-based flame retardant agents of the prior art, thereby providing an advantage whereby flame retardant treating can be accomplished without lowering the original properties of the thermoplastic polymer.

Furthermore, the flame retardant phosphorus-based compounds represented by formula (1) above and their salts have high thermal stability and do not adversely affect the production process (thermoforming, etc.) for plastic materials such as thermoplastic polymers, while the risk of escape by volatilization and the like during the conditions of ordinary thermoforming is also eliminated.

At least one type of melamine-based compound, such as a melamine condensation product, the reaction product of melamine and phosphoric acid, or the reaction product of a melamine condensation product and phosphoric acid, is preferably also included. Such melamine-based compounds can impart a certain degree of flame retardance to plastic materials by themselves, as mentioned above, but it has been confirmed that if they are used in combination with phosphorus-compounds represented by formula (1), even greater flame retardance is achieved than by conventional synergistic combinations when the treated article is a thermoplastic polymer.

The term "thermoplastic polymer" used according to the invention refers to a polymer, either having no side chains or having side chains of various lengths and numbers, that can be molded into virtually any shape when softened by heating, as explained by Hans Domininghaus on page 14 of "Die Kunststoffe und ihre Eigenschaften", 5th Edition (1988).

The salt of a phosphorus-based compound represented by formula (1) is preferably an alkali metal salt, alkaline earth metal salt, aluminum salt, zinc salt, ammonium salt or amine salt. It was found that using these salts gives significantly and notably higher flame retardance to flame retardant treated articles compared to other salts.

The flame retardant treating process of the invention comprises a flame retardant treating agent providing step wherein fiber is treated with a flame retardant treating agent according to claim 1, and a heat treatment step wherein the fiber treated with the flame retardant treating agent is subjected to heat. As mentioned above, this heat treatment promotes infiltration and fixing of the flame retardant treating agent into the fibers.

Specifically, in the heat treatment step the fiber is preferably heat treated to a temperature in the range of 100–220° C. to fix the flame retardant treating agent onto the fiber. When the temperature is at least 100° C., the amorphous regions of the fiber molecules tend to relax or expand to an extent allowing the molecules or particles of the phosphorus-based compound represented by formula (1) to sufficiently infiltrate the fiber, thereby increasing the coverage of the flame retardant treating agent. When the heat treatment temperature is 220° C. or below, fiber strength reduction and heat deformation can be easily prevented.

More preferably, the fiber may be immersed in a first treatment solution containing the flame retardant treating agent to treat the fiber with the flame retardant treating agent in the flame retardant treating agent providing step, and then the first treatment solution may be heated to a temperature in the range of 90–150° C. in the heat treatment step to fix the flame retardant treating agent onto the fiber.

When this mode is employed, the phosphorus-based compound attached to the fiber surface infiltrates and is fixed to the fiber interior by wet heat treatment accomplished by heating of the first treatment solution. When the temperature of the first treatment solution, i.e. the heat treatment temperature, is at least 90° C., the phosphorus-based compound easily infiltrates into the amorphous regions of the fiber molecules, as explained above. On the other hand, when the heat treatment temperature is 150° C. or below, it is possible to prevent fiber strength reduction and heat deformation. In this case, the fiber may be immersed into a preheated first treatment solution.

Alternatively, and even more preferably, the fiber is immersed in a second treatment solution containing the flame retardant treating agent and a carrier to treat the fiber with the flame retardant treating agent in the flame retardant treating agent providing step, and then the second treatment solution is heated to a temperature in the range of 80–130° C. in the heat treatment step to fix the flame retardant treating agent onto the fiber.

When this mode is employed, the carrier swells the fiber, thus promoting fixing of the flame retardant treating agent into the molecular configuration of the fiber. A sufficient amount of the flame retardant treating agent may thus be fixed into the fiber even with heating in a gentle temperature range (such as 80–130° C.). Furthermore, since the treatment temperature can thus be lowered, strength reduction and heat deformation of the fiber are further prevented and energy consumption is thereby reduced. In this case, the fiber may be immersed into a preheated second treatment solution.

According to another mode, the flame retardant treating process of the invention comprises a flame retardant treating agent providing step in which a thermoplastic polymer is treated with a flame retardant treating agent according to the invention. As explained above, a flame retardant treating agent of the invention comprising one of the aforementioned melamine-based compounds in addition to phosphorus-based compound represented by formula (1) or a salt thereof is highly advantageous for imparting flame retardance to thermoplastic polymers.

In this case, particularly preferred thermoplastic polymers to be imparted with flame retardance according to the invention include HIPS (high-impact polystyrene), polyphenylene ether, polyamide, polyester, polyethylene, polypropylene, polycarbonate, ABS (acrylonitrile-butadiene-styrene), PC/ABS (polycarbonate/acrylonitrile-butadiene-styrene) blend and PPE/HIPS (polyphenylene ether/high-impact polystyrene) blend. That is, flame retardant treated articles with excellent flame retardance can be obtained using these materials as the articles to be treated. In other words, the present invention is an excellent process for producing flame retardant treated articles by accomplishing flame retardant treating of these thermoplastic polymers.

More specifically, and more preferred in the flame retardant treating agent treatment process, a phosphorus-based compound and/or its salt is used in a concentration range of 1–30 wt % with respect to the thermoplastic polymer, while a melamine-based compound is also used in a concentration range of 1–30 wt % with respect to the thermoplastic polymer.

If the proportion of the phosphorus-based compound and/or its salt used and the proportion of the melamine-based compound used are both at least 1 wt % with respect to the thermoplastic polymer to be treated, the synergistic effect of both will be significantly exhibited to impart sufficient flame retardance to the thermoplastic polymer. On the other hand, if their proportions are both 30 wt % or below, the risk of impairment of the moldability of the thermoplastic polymer is reduced, and deformation may therefore be minimized.

The flame retardant treated article of the invention is characterized by comprising a polymer material, specifically fiber, having fixed therein a phosphorus-based compound represented by formula (1) and/or its salt. Alternatively, the flame retardant treated article of the invention is characterized by comprising a polymer material, specifically a thermoplastic polymer, having fixed or included therein a phosphorus-based compound represented by formula (1) and/or its salt, or a phosphorus-based compound and/or its salt as well as at least one type of melamine-based compound selected from among melamine condensation products, reaction products of melamine and phosphoric acid and reaction products of melamine condensation products and phosphoric acid. Phosphorus-based compound salts are preferably alkali metal salts, alkaline earth metal salts, aluminum salts, zinc salts, ammonium salts or amine salts.

The present invention will become more fully understood from the detailed description given hereinbelow and the accompanying drawings which are given by way of illustration only, and thus are not to be considered as limiting the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

Preferred embodiments of the flame retardant treating agents, flame retardant treating process and flame-retardant treated articles of the invention will now be described.

[Flame Retardant Treating Agent]

(Component A)

A flame retardant treating agent comprises a phosphorus-based compound represented by the following formula (1) and/or its salt (hereinafter referred to as ("component A"). Agents comprising mainly component A as the flame retardant component are particularly suited for flame retardant treatment of fiber.

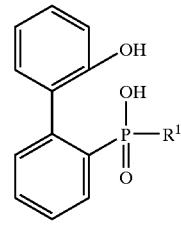

(1)

wherein $R^1$ represents an alkyl, hydroxyalkyl or substituted or unsubstituted aralkyl group, with $R^1$ most preferably having a total carbon number of 1–12, or a group represented by the following formula (2):

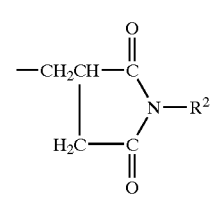

(2)

wherein $R^2$ represents an alkyl group of 1–10 carbons.

Preferred as phosphorus-based compound salts for component A are salts of the phosphorus-based compounds represented by formula (1) with alkali metals, alkaline earth metals, aluminum, zinc, ammonia and amines, with preferred amines being amines having a total carbon number of 2–9 and alkanolamines. More specific examples of component A are the compounds represented by the following formulas (3) to (6).

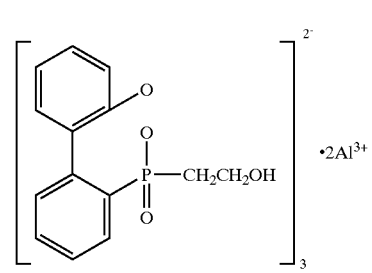

(3)

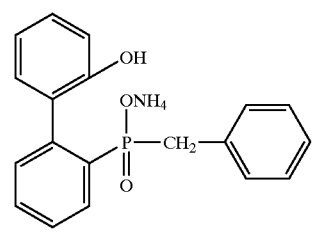

(4)

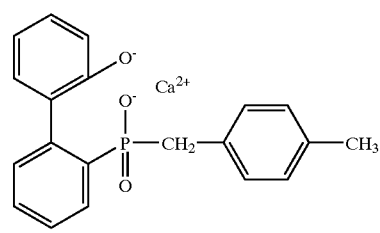

(5)

-continued

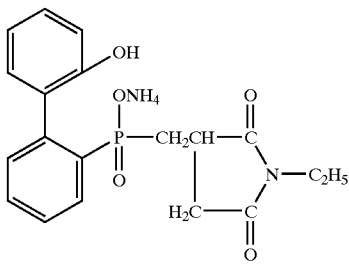

(6)

The compounds for component A may be produced by treatment, such as hydrolysis, of compounds obtained by the production processes described in Japanese Examined Patent Publication SHO No. 50-17979, Japanese Unexamined Patent Publication SHO No. 55-124792 and Japanese Examined Patent Publication SHO No. 56-9178.

The flame retardant treating agent of the invention may be supplied in a variety of forms, and particularly, component A is preferably supplied as a powder, as an aqueous solution thereof dissolved, emulsified or dispersed in water, or as a solution or dispersion thereof in an organic solvent, although in terms of environmental considerations it is preferably supplied in the form of an aqueous solution or an emulsified or dispersed aqueous liquid.

As emulsifying and dispersing agents there may be used conventionally employed emulsifying and dispersing agents, specific examples of which include nonionic surfactants, for example, polyalkyleneglycol types such as higher alcohol alkylene oxide addition products, alkylphenol alkylene oxide addition products, styrenated alkylphenol alkylene oxide addition products, styrenated phenol alkylene oxide addition products, fatty acid alkylene oxide addition products, polyhydric alcohol fatty acid ester alkylene oxide addition products, higher alkylamine alkylene oxide addition products, fatty acid amide alkylene oxide addition products, fat alkylene oxide addition products and polypropylene glycol ethylene oxide addition products, and polyhydric alcohol types such as glycerol fatty acid esters, pentaerythritol fatty acid esters, sorbitol and sorbitan fatty acid esters, sucrose fatty acid esters, polyhydric alcohol alkyl ethers, alkanolamine fatty acid amides, and the like.

Alternatively, there may be used anionic surfactants, for example, carboxylic acid salts such as fatty acid soaps, sulfuric acid esters such as higher alcohol sulfuric acid esters, higher alkyl polyalkylene glycol ether sulfuric acid esters, sulfated oils, sulfated fatty acid esters, sulfated fatty acids and sulfated olefins, formalin condensates of alkylbenzenesulfonic acid salts, alkylnaphthalenesulfonic acid salts, naphthalenesulfonic acid, sulfonic acid salts such as α-olefin sulfonic acid salts, paraffin sulfonic acid salts, Igepon T types and sulfosuccinic acid diesters, and phosphoric acid esters such as higher alcohol phosphoric acid esters.

For a dispersion, dispersion stabilizers such as polyvinyl alcohol, methylcellulose, carboxymethyl cellulose, hydroxyethyl cellulose, xanthan gum and starch paste may be used.

The content of an emulsifier or dispersing agent (dispersion stabilizer) is preferably 0.05–5 wt % and more preferably 0.1–3 wt % with respect to the total weight of the flame retardant treating agent. If the content of the dispersion stabilizer is less than 0.05 wt %, aggregation or precipitation of component A tends to be insufficiently controlled. If, on the other hand, the content is greater than 5 wt %, the viscosity of the dispersion increases, thus tending to lower the treatability of the fibers or other treated article with the flame retardant treating agent. The average molecular weight of the emulsifier or dispersing agent is preferably selected as appropriate to prevent aggregation or precipitation of component A in the content range mentioned above.

The organic solvent used for provision in the form of a solution of component A in an organic solvent is not particularly restricted so long as it dissolves the phosphorus-based compound or salt thereof used as component A, and examples include alcohols such as methanol, ethanol and isopropanol, aromatic hydrocarbons such as benzene, toluene and xylene, ethers such as dioxane and ethylene glycol, amides such as dimethylformamide and sulfoxides such as dimethylsulfoxide, while combinations of two or more of these may also be used.

When the flame retardant treating agent of the invention is in an emulsified or dispersed aqueous liquid, there may be used an emulsifying or dispersing machine such as a homogenizer, colloid mill, ball mill, sand grinder or the like, as conventionally employed for production of emulsion or dispersion type flame retardant treating agents. The mean particle size of the phosphorus-based compound particles in the flame retardant treating agent is preferably no greater than 10 μm. A mean particle size of 10 μm or less will facilitate emulsification or dispersion of component A by the aforementioned emulsifying or dispersing agent.

(Component B)

The flame retardant treating agent of the invention also usefully comprises, in addition to component A, also at least one type of melamine-based compound (hereinafter referred to as "component B") selected from among melamine condensation products, reaction products of melamine and phosphoric acid and reaction products of melamine condensation products and phosphoric acid. Compounds comprising component A and component B as flame retarding components are particularly suited for flame retardant treatment of plastics, and especially thermoplastic polymers.

Preferred as melamine condensation products for component B include any selected from among melem, melam, melon and their higher condensed compounds. As reaction products of melamine condensation products and phosphoric acid for component B there may be mentioned as preferred dimelamine pyrophosphate, melamine polyphosphate, melem polyphosphate, melam polyphosphate, and their mixed poly salts (for example, the mixed poly salts described in the International Patent Application PCT/WO98/39306 pamphlet and elsewhere).

These reaction products of melamine condensation products and phosphoric acid are publicly known from the relevant literature, and can be produced by methods other than direct reaction with phosphoric acid as described above. For example, melamine polyphosphate may be produced by reaction of polyphosphoric acid and melamine as described in the International Patent Application PCT/WO98/45364 pamphlet, or it may be produced by condensation of melamine phosphate or melamine pyrophosphate as described in the International Patent Application PCT/WO98/08898.

[Flame Retardant Treating Process]

A concrete example of a process for obtaining flame retardant treated articles using the flame retardant treating process of the invention will now be explained. The aforementioned flame retardant treating agents of the invention are not particularly restricted in their target of application, but are particularly useful for polymer materials such as fibers and thermoplastic polymers including plastics. Modes of flame retardant treatment of fiber and of thermoplastic polymers will each be described in detail.

(Fiber Flame Retardant Treating Process)

This process employs fiber as the treated article to obtain flame retardant treated fiber (flame retardant treated article), treating the fiber with a flame retardant treating agent containing component A as the major component (flame retardant treating agent providing step) and heating the fiber for post-treatment (heat treatment step). The type of fiber used is not particularly restricted and may be synthetic fiber such as polyester, nylon, acryl or polyurethane, semi-synthetic fiber such as acetate, regenerated fiber such as rayon, natural fiber such as cotton, hemp, silk or wool, and their composite fibers, among which polyester fiber is especially useful for the invention. There are also no particular restrictions on the form of the fiber, among which there may be mentioned various fiber products such as yarn, woven fabrics, knitted fabrics, nonwoven fabrics, thread, rope and the like.

The flame retardant treating process may be, for example, if the fiber is synthetic fiber or semi-synthetic fiber, a process in which, prior to spinning of the fiber, a phosphorus-based compound represented by formula (1) or its salt, as the flame retarding component of the flame retardant treating agent, is mixed with the molten polymer of the fiber which is then spun.

When flame retardance is imparted to the fiber during spinning, in the case of polyester fiber, for example, the flame retardant treating agent is preferably added for P (phosphorus atom) content in the polyester fiber of at least 0.2 wt %, preferably 0.3–3.0 wt % and especially 0.5–1.5 wt %. If the P content is less than 0.2 wt %, the flame retardance will tend to be lacking. On the other hand, if the P content is greater than 3.0 wt %, the flame retardant effect becomes saturated while the original properties of the polyester fiber may be impaired. There are no particular restrictions on the spinning temperature or spinning speed, and conventional spinning conditions may be applied. There are also no particular restrictions on the type of fiber, and in the case of polyester fiber, for example, regular polyester fiber, cationic dyeable polyester fiber and the like may be used.

In the case of fiber, flame retardant treating may be carried out by post-treatment, in which case one of the three types of processes described below is preferably employed. These flame retardant treating processes will be explained using polyester fiber woven fabric as the specific object. Regardless of the process, however, there are no restrictions on the type of fiber, as with treatment accomplished during spinning. In the case of polyester fiber, for example, there may be used regular polyester fiber, cationic dyeable polyester fiber and the like.

(First Process)

The first process is a process wherein the polyester fiber woven fabric is treated with a flame retardant treating agent by a flame retardant treating agent providing step, and then the polyester fiber woven fabric is subjected to heat treatment at a prescribed temperature, the process employed being a dry heating or wet heating process involving a spray treating/dry curing system, a padding/drying/steaming system, a padding/steaming system, a padding/drying/curing system, or the like. More specifically, the polyester fiber woven fabric is first subjected to spray treatment or padding treatment with the treatment solution which contains the flame retardant treating agent and may be optionally diluted, and is then dried, after which it is heat treated in a temperature range of preferably 100–220° C. and more preferably 160–190° C., for a period of, for example, 10 or more seconds or a few minutes.

If the temperature is below 100° C., the amorphous regions of the molecules of the polyester fiber may not relax or expand enough to receive the phosphorus-based compound molecules or particles. A higher heat treatment temperature can result in firmer attachment of the flame retardant treating agent to the polyester fiber woven fabric, but if the heat treatment temperature exceeds 220° C. in the first process, the fiber strength of the polyester woven fabric may be reduced or heat deformation may occur, although this will depend on differences in the heating time. Consequently, carrying out the heat treatment step in the preferred temperature range described above allows stable and more attachment of the phosphorus-based compound and/or its salt in the flame retardant treating agent to the amorphous regions of the polyester fiber molecules. As a result, it is possible to achieve sufficient flame retardance and cleaning durability for polyester fiber woven fabrics.

(Second Process)

The second process is a process wherein a polyester fiber woven fabric is treated with the flame retardant treating agent in the flame retardant treating agent providing step by immersing the polyester fiber in a treatment solution which contains the flame retardant treating agent and may be optionally diluted (first treatment solution), while heating the treatment solution for heat treatment of the polyester fiber woven fabric at a prescribed temperature. That is, the flame retardant treating agent providing step and heat treatment step are carried out simultaneously in this process.

Specifically, a package dyeing machine such as a liquid-flow dyeing machine, beam dyeing machine or cheese dyeing machine may be used for immersion heat treatment at a temperature of preferably 90–150° C. and more preferably 110–140° C., for several minutes to ten or more minutes, with the polyester fiber woven fabric immersed in the first treatment solution, in order to fix the flame retardant treating agent onto the polyester fiber woven fabric.

If the temperature is below 90° C., the amorphous regions of the polyester fiber molecules may not relax or expand enough to receive the phosphorus-based compound molecules or particles. On the other hand, if the temperature is above 150° C., the fiber strength of the polyester fiber woven fabric may be reduced or heat deformation may occur, although this will differ depending on the heating time. In this second process as well, therefore, carrying out the heat treatment step in the preferred temperature range described above allows stable and more attachment of the phosphorus-based compound and/or its salt of the flame retardant treating agent to the amorphous regions of the polyester fiber molecules. As a result, it is possible to achieve sufficient flame retardance and cleaning durability for polyester fiber woven fabrics. Incidentally, a similar excellent flame retardant treating agent-fixing effect can also be achieved by preheating the first treatment solution to the aforementioned temperature before immersing the polyester fiber woven fabric.

(Third Process)

The third process is a process wherein a polyester fiber woven fabric is treated with the flame retardant treating agent in the flame retardant treating agent providing step by immersing the polyester fiber woven fabric in a treatment solution which contains the flame retardant treating and a carrier and may be optionally diluted (second treatment solution), while heating the second treatment solution for heat treatment of the polyester fiber woven fabric at a prescribed temperature. The third process is therefore a process in which the flame retardant treating agent providing step and heat treatment step are carried out simultaneously, similar to the second process described above. The carrier used here may be a carrier conventionally employed for carrier dyeing, and for example, there may be used chlorbenzene-based, aromatic ester-based, methylnaphthalene-based, diphenyl-based, benzoic acid-based or orthophenylphenol-based compounds, either alone or in combinations of two or more.

In the third process, the carrier emulsified or dispersed in the second treatment solution swells the polyester fiber, thereby promoting satisfactory fixing of the flame retardant treating agent into the molecular configuration of the polyester fiber woven fabric. As a result, it is possible to accomplish stable fixing of an adequate amount of the flame retardant treating agent onto the polyester fiber woven fabric even with heat treatment under gentler heating conditions, i.e., low temperature conditions of preferably 80–130° C. Because of the low heating temperature, it is possible to adequately prevent strength reduction or heat deformation of the polyester fiber woven fabric during the heat treatment step. A second treatment solution may be heated to the aforementioned preferred temperature prior to immersion of the polyester fiber woven fabric.

The carrier content is preferably 0.1–10% o.w.f. ("on the weight of fiber", same hereunder) and more preferably 1.0–5.0% o.w.f, with respect to the weight of the treated polyester fiber woven fabric. If the carrier content is below the lower limit of this range, fixing of the flame retardant treating agent onto the polyester fiber woven fabric may not be sufficiently promoted, while if it is above the higher limit of this range, the carrier may not easily emulsify or disperse in the treatment solution.

For satisfactory emulsification or dispersion of the carrier in the treatment solution, there may be appropriately added to the treatment solution a surfactant such as sulfated castor oil, an alkylbenzenesulfonic acid salt, a dialkylsulfosuccinic acid salt, polyoxyethylene (POE) castor oil ether, a POE alkylphenyl ether, or the like.

According to the invention, the amount of the phosphorus-based compound fixed to the fiber, in the case of polyester fiber, is preferably 0.05–30 wt % and more preferably 1–15 wt % with respect to the total amount of polyester fiber containing the phosphorus-based compound, although this will differ depending on the type, form, etc. of the fiber. If the fixing amount of the phosphorus-based compound onto the polyester fiber is less than 0.05 wt %, it becomes impossible to impart a sufficient degree of flame retardance to the polyester fiber. On the other hand, if the fixing amount exceeds 30 wt %, there is no notable increase in the flame retarding effect corresponding to the increased portion of the phosphorus-based compound, and instead, the feel of the polyester fiber will tend to be impaired and exhibit a hard feel.

In the second and third processes described above, the flame retardant treating agent may be fixed to the polyester fiber woven fabric by immersion heat treatment (flame retardant treating agent providing step+heat treatment step) at any stage before, during or after dyeing of the polyester fiber woven fabric, but it is preferably carried out simultaneously with dyeing from the standpoint of reducing the number of operating steps (working stages) for increased operating efficiency.

In the first to third processes described above, the heat treatment step is preferably followed by soaping treatment of the polyester fiber woven fabric by a common method, for removal of the phosphorus-based compound which is not firmly fixed to the polyester fiber woven fabric but merely gently (loosely) adhering to the surface thereof. The detergent used for the soaping treatment may be a common anionic, nonionic or amphoteric surfactant, or a mixture thereof.

To obtain a polyester fiber woven fabric requiring no cleaning durability, it is sufficient to merely attach the phosphorus-based compound in the flame retardant treating agent onto the polyester fiber woven fabric, in which case the heat treatment step may be omitted. A flame retardant property can be adequately imparted even to a polyester fiber woven fabric prepared in this manner.

When the obtained flame retardant treated fiber must exhibit light fastness or other properties in addition to flame retardance, benzotriazole-based or benzophenone-based ultraviolet absorbers or other fiber treatment agents used in the prior art may be added with the flame retardant treating agent so long as the flame retardant property is not impaired. As possible fiber treatment agents there may be mentioned antistatic agents, water repellent agents, stain-proofing agents, hardness finishers, texture adjustors, softeners, antibacterial agents, hygroscopic agents, anti-slip agents and the like.

(Thermoplastic Polymer Flame Retardant Treating Process)

This process employs a thermoplastic polymer as the treated article to obtain flame retardant treated plastic (flame retardant treated article), treating it with a flame retardant treating agent of the invention containing component A or components A and B as the major components (flame retardant treating agent providing step). The type of thermoplastic polymer used is not particularly limited, and for example, there may be mentioned those described in the International Patent Application PCT/EP97/01664 pamphlet. These include, specifically, the following.

(1) Monoolefin or diolefin polymers (for example, polypropylene polyisobutylene, polybutylene, poly-1-butene, polyisoprene, polybutadiene, etc.), cycloolefin polymers (for example, cyclopentene and norbornane polymers), and in some cases optionally crosslinked polyethylene (for example, high-density polyethylene (HDPE), high-density/high molecular weight polyethylene (HDPE-HMW), high-density/ultrahigh molecular weight polyethylene (HDPE-UHMW), medium-density polyethylene (MDPE), low-density polyethylene (LDPE), linear low-density polyethylene (LLDPE) and branched very low-density polyethylene (VLDPE)).

(2) Mixtures of the polymers listed in (1) above, for example, mixtures of polypropylene and polyisobutylene, mixtures of polypropylene and polyethylene (for example, PP/HDPE or PP/LDPE) and mixtures of various grades of polyethylene (for example, LDPE/HDPE).

(3) Mono- or diolefin copolymers, copolymers of mono- or diolefin and other vinyl monomers (for example, ethylene-propylene copolymer or linear low-density polyethylene (LLDPE)), mixtures of these with low-density polyethylene (LDPE), propylene-1-butene copolymer, propylene-isobutylene copolymer and ethylene-1-butene copolymer, or ethylene-alkyl acrylate copolymers, ethylene-vinyl acetate copolymer, copolymers of these with carbon monoxide, ethylene-acrylic acid copolymer, salts thereof (ionomers), terpolymers of ethylene, propylene and dienes (for example, hexadiene, dicylcopentadiene or ethylidenenorbornane), mixtures of more than one of these copolymers, mixtures of these copolymers with the polymers listed in (1) above (for example, polypropylene/ethylene-propylene copolymer, LDPE/ethylene-vinyl acetate copolymer, LDPE/ethylene-acrylic acid copolymer, LLDPE/ethylene-vinyl acetate copolymer or LLDPE/ethylene-acrylic acid copolymer), polyalkylene-carbon monoxide copolymer having an alternating sequence or random sequence structure, and copolymers of these with other polymers (for example, mixtures with polyamides or the like).

(4) Polystyrene, poly(p-methylstyrene), poly(α-methylstyrene).

(5) Copolymers of styrene or α-methylstyrene and dienes or acrylate compounds (for example, styrene-butadiene, styrene-acrylonitrile, styrene-alkyl methacrylate, styrene-butadiene-alkyl acrylate, styrene-butadiene alkyl methacrylate, styrene-maleic anhydride or styrene-acrylonitrile-methacrylate), high-impact mixtures prepared from styrene copolymer and other polymers (for example, polyacrylates, diene polymers or ethylene-propylene-diene terpolymers), styrene block copolymers (for example, styrene-butadiene-styrene, styrene-isoprene-styrene, styrene-ethylene/butylene-styrene or styrene-ethylene/propylene-styrene).

(6) Styrene or α-methylstyrene graft copolymers (for example, styrene-grafted polybutadiene, styrene-grafted polybutadiene-styrene copolymer, polybutadiene-acrylonitrile copolymer, styrene- and acrylonitrile- or methacrylonitrile-grafted polybutadiene), styrene-, acrylonitrile- and methyl methacrylate-grafted polybutadiene, styrene- and maleic anhydride-grafted polybutadiene, styrene-, acrylonitrile- and maleic anhydride- or maleic imide-grafted polybutadiene, styrene- and maleimide-grafted polybutadiene, styrene- and alkyl acrylate- or alkyl methacrylate-grafted polybutadiene, styrene- and acrylonitrile-grafted ethylene-propylene-diene terpolymer, styrene- and acrylonitrile-grafted polyalkyl acrylate or polyalkyl methacrylate, styrene- and acrylonitrile-grafted acrylate-butadiene copolymer, or mixtures of these with the polymers listed in (5) above, as for example, ABS polymer, MBS polymer, ASA polymer or AES polymer.

(7) Polymers derived from α,β-unsaturated acids or their derivatives (for example, polyacrylate and polymethacrylate, butyl acrylate-impact-modified polymethyl methacrylate, polyacrylamide or polyacrylonitrile).

(8) Copolymers of the monomers listed in (7) above or copolymers of these monomers with other unsaturated monomers (for example, acrylonitrile-butadiene copolymer, acrylonitrile-alkyl acrylate copolymers, acrylonitrile-alkoxyalkyl acrylate copolymers, acrylonitrile-vinyl halide copolymers or acrylonitrile-alkyl methacrylate-butadiene terpolymers).

(9) Polymers of unsaturated alcohols and amines, or their acetyl derivatives or acetal-derived polymers (for example, polyvinyl alcohol, polyvinyl acetate, polyvinyl stearate, polyvinyl benzoate, polyvinyl maleate, polyvinyl butyral, polyallyl phthalate, polyallyl melamine), or copolymers of these with the olefins listed in (1) above.

(10) Polyacetals (for example, polyoxymethylene and comonomer (for example, ethylene oxido)-containing polyoxymethylene), thermoplastic polyurethanes, acrylates, MBS-modified polyacetals, etc.

(11) Polyphenylene oxidos, polyphenylene sulfidos and mixtures of these oxidos or sulfidos with styrene polymers or polyamides.

(12) Diamine and dicarboxylic acid and/or aminocarboxylic acid or corresponding lactam-derived polyamides and copolyamides (for example, nylon-4, nylon-6, nylon-6,6, nylone-6,10, nylon-6,9, nylon-6,12, nylon-4,6, nylon-12, 12, nylon-11, nylon-12, m-xylene, diamine- and adipic acid-based aromatic polyamides, polyamides produced from hexamethylenediamine and iso-and/or terephthalic acid, and if necessary an elastomer as a modifier (for example, poly-2,4,4-trimethylhexamethylene terephthalamide and poly-m-phenyleneisophthalamide)), block copolymers of these polyamides with polyolefins, olefin copolymers, ionomers or chemically bonded or grafted elastomers, block copolymers of these polyamides with polyethers (for example, polyethylene glycol, polypropylene glycol and polytetramethylene glycol), and EPDM- or ABS-modified polyamides or copolyamides, and polyamides which are condensed during processing treatment ("IM polyamide systems").

(13) Polyurea, polyimides, polyamidoimides, polyetherimides, polyesterimides, polyhydantoin, polybenzimidazole, etc.

(14) Dicarboxylic acid and dialcohol and/or hydroxycarboxylic acid or corresponding lactone-derived polyesters (for example, polyethylene terephthalate, polybutylene terephthalate, poly-1,4-dimethylolcyclohexane terephthalate, polyhydroxybenzoate and block polyether esters derived from hydroxy terminal group-containing polyethers), polycarbonate- or MBS-modified polyesters.

(15) Polycarbonate, polyester carbonate, etc.

(16) Polysulfone, polyethersulfone, polyetherketone, etc.

(17) Mixtures of the above-mentioned polymers (polymer blends: for example, PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylate, POM/thermoplastic PU, PC/thermoplastic PU, POM/acrylate, POM/MBS, PPO/HIPS, PPO/nylon-6,6, copolymers, etc.

Among the aforementioned thermoplastic polymers which are suitable for using flame retardant treating agents of the invention comprising component A or component A and component B, there may be mentioned as preferable, for example, HIPS (high-impact polystyrene), polyphenylene ether, polyamide, polyester, polyethylene, polypropylene, polycarbonate, ABS (acrylonitrile-butadiene-styrene), PC/ABS (polycarbonate/acrylonitrile-butadiene-styrene) blend and PPE/HIPS (polyphenylene ether/high-impact polystyrene) blend or polymer blends. "High-impact polystyrene" is polystyrene having impact strength which is higher than ordinary.

As an example of a method for treating such thermoplastic polymers with a flame retardant treating agent of the invention comprising component A or component A and component B, first all of the components of the flame retardant treating agent are mixed in a mixer in powder or pellet form, and then they are added to the molten polymer in a blender (for example, a twin-screw extruder or the like) and mixed to uniformity for introduction into the thermoplastic polymer. The melt obtained thereby is usually drawn out as an extract and cooled to make pellets. Instead of adding component A or component A and component B, each may be independently introduced into the blender using a batch addition system.

Also, component A or component A and component B may be combined with previously prepared thermoplastic polymer pellets or powder and the mixture directly processed with an injection molding machine to obtain a plastic molded article. For example, when a polyester is used as the thermoplastic polymer, component A or component A and component B may be added to the polyester composition during the polyester polycondensation process.

Component A, or component A and component B, may be used in a variety of forms depending on the nature of the thermoplastic polymer to be treated and the desired polymer properties. For example, from the standpoint of achieving satisfactory dispersion, a thermoplastic polymer in fine particulate form obtained by pulverization of component A or component A and component B is preferred.

Reinforcers such as fillers or glass fibers and minerals such as glass beads or chalk may be added to the thermoplastic polymer molding material as other components of the flame retardant treating agent or components separate from the flame retardant treating agent. Other additives, such as antioxidants, photostabilizers, lubricants, coloring agents, nucleating agents, antistatic agents and the like may also be included. Additives which may be used include those mentioned in European Patent Application Publication No. 584,567.

To the knowledge of the present inventors, the flame retardance of a thermoplastic polymer is increased more when using a relatively high molecular weight melamine derivative and/or its phosphoric acid reaction product as component B together with component A, than when using a lower molecular weight melamine derivative such as melamine cyanurate or melamine phosphate as component B together with component A. Furthermore, it has been confirmed the flame retardant treating agents of the invention which comprise both component A and component B exhibit a stronger synergistic effect than phosphinic acid salts alone or mixtures containing them described in the aforementioned International Patent Application PCT/EP97/01664 pamphlet, German Patent Application Publication No.19734437 and German Patent Application Publication No.19737727.

The amount of the flame retardant treating agent used in the flame retardant treating agent providing step will differ depending on the nature of the thermoplastic polymer and the type of component A and component B, but component A (phosphorus-based compound represented by formula (1) and/or its salt) is preferably used at 1–30 wt %, more preferably 3–20 wt % and even more preferably 3–15 wt % with respect to the thermoplastic polymer. Component B (melamine-based compound) is preferably used at 1–30 wt %, more preferably 3–20 wt % and even more preferably 3–15 wt % with respect to the thermoplastic polymer, independently from component A.

If the proportion of component A and component B used is greater than 1 wt %, the synergistic effect of the two components is exhibited to a significant degree and sufficient flame retardance can be easily imparted to the thermoplastic polymer. If the proportion of the components is 30 wt % or below, the risk of impairment of the molding workability of the thermoplastic polymer is reduced, and its degeneration can be prevented.

[Flame Retardant Treated Articles]

As mentioned above, flame retardant treated articles according to the invention are polymer materials that have been treated with a flame retardant treating agent of the invention, and specifically there may be mentioned fibers which have been flame retardant treated by the flame retardant treating process of the invention (flame retardant treated fibers) and plastics such as thermoplastic polymers which have been flame retardant treated by the flame retardant treating process of the invention (flame retardant plastic molding materials).

Flame retardant treated fibers may be in any form including yarn, woven fabrics, knitted fabrics, nonwoven fabrics and the like. Flame retardant plastic molding materials may be in the form of moldings, films, filaments or fibers, and may be worked into desired products by common plastic working such as, for example, injection molding, extrusion molding, press molding and the like.

EXAMPLES

The present invention will now be explained in greater detail by way of the following examples, which are not intended to be limitative on the invention.

Example 1

To 40 g of the phosphorus-based compound represented by formula (3) above as component A there was added as a dispersing agent 5 g of an ethylene oxide 10 molar addition product of tristyrenated phenol, and then 53 g of water was added thereto while stirring. Next, 2 g of a 10 wt % aqueous solution of carboxymethyl cellulose was added as a dispersion stabilizer to obtain a flame retardant treating agent as a white dispersion.

Example 2

A flame retardant treating agent was obtained as a white dispersion in the same manner as Example 1, except that the phosphorus-based compound represented by formula (4) was used as component A instead of the phosphorus-based compound represented by formula (3).

Example 3

A flame retardant treating agent was obtained as a white dispersion in the same manner as Example 1, except that the phosphorus-based compound represented by formula (5) was used as component A instead of the phosphorus-based compound represented by formula (3).

Example 4

A flame retardant treating agent was obtained as a white dispersion in the same manner as Example 1, except that the phosphorus-based compound represented by formula (6) was used as component A instead of the phosphorus-based compound represented by formula (3).

Example 5

To 40 g of the phosphorus-based compound represented by formula (4) as component A there was added as a dispersing agent 5 g of a compound obtained by adding 10 moles of ethylene oxide to tristyrenated phenol and sulfonating the product, and then 53 g of water was added thereto while stirring. Next, 2 g of a 10 wt % aqueous solution of xanthan gum was added as a dispersion stabilizer to obtain a flame retardant treating agent as a white dispersion.

Example 6

A flame retardant treating agent was obtained by adding and dissolving 90 g of methanol in 10 g of the phosphorus-based compound represented by formula (4) as component A.

Comparative Example 1

To 40 g of hexabromocyclododecane there was added as a dispersing agent 5 g of an ethylene oxide 20 molar addition product of tristyrenated phenol, and then 53 g of water was added thereto while stirring. Next, 2 g of a 10 wt % aqueous solution of carboxymethyl cellulose was added as a dispersion stabilizer to obtain a flame retardant treating agent as a white dispersion.

(Flame Retardant Treating of Polyester Fiber Woven Fabric)

A polyester fiber woven fabric with a basis weight of 103 g/m², obtained using 75 denier/36 filament warp yarn and 105 denier/53 filament weft yarn composed of polyethylene terephthalate at a warp thread count of 8000/m and a weft thread count of 3200/m, was subjected to flame retardant treatment by the following treatment methods A, B and C, using the flame retardant treating agents obtained in Examples 1–6 and Comparative Example 1.

[Treatment Method A]

The polyester fiber woven fabric was subjected to padding treatment (70% contraction) with a treatment solution diluted to contain one of the phosphorus-based compounds (Examples 1–6) or hexabromocyclododecane (Comparative Example 1) as the flame retardant treating agent at 8 wt %, and was then dried at 110° C. for 5 minutes and subjected to heat setting treatment at 190° C. for 60 seconds.

[Treatment Method B]

The polyester fiber woven fabric was immersed in a treatment solution diluted to contain 1% o.w.f. of a disperse dye (C.I. Disperse Blue 56), 0.5 g/L of the dispersion level dyeing agent RM-EX (product of Nicca Chemical Co., Ltd.) and 6% o.w.f. of one of the phosphorus-based compounds (Examples 1–6) or hexabromocyclododecane (Comparative Example 1) as the flame retardant treating agent, to a liquor ratio of 1:15, and then a Minicolor Dyeing Machine (product of Texam Giken) was used for heat treatment at 130° C. for 30 minutes. The fabric was then subjected to reduction cleaning in an aqueous solution containing 1 g/L of the soaping agent Escudo FR (product of Nicca Chemical Co., Ltd.), 2 g/L of hydrosulfite and 1 g/L of caustic soda at 80° C. for 20 minutes, and after warm water washing and cold water washing, it was dried at 120° C. for 2 minutes.

[Treatment Method C]

The polyester fiber woven fabric was immersed in a treatment solution diluted to contain 1% o.w.f. of a disperse dye (C.I. Disperse Blue 56), 3% o.w.f. of benzoic acid as a carrier and 6% o.w.f. of one of the phosphorus-based compounds (Examples 1–6) or hexabromocyclododecane (Comparative Example 1) as the flame retardant treating agent, to a liquor ratio of 1:15, and then a Minicolor Dyeing Machine (product of Texam Giken) was used for heat treatment at 110° C. for 30 minutes. The fabric was then subjected to reduction cleaning in the same manner as Treatment method B, and after warm water washing and cold water washing, it was dried at 110° C. for 5 minutes.

(Flame Retardant Property Test 1)

The flame retardant treated polyester fiber woven fabrics obtained by treatment methods A to C described above (flame retardant treated fibers) were subjected to a flameproof performance test conducted according to Method A-1 and Method D specified by JIS L1091 (1999). The flameproof performance test was evaluated for flame retardant treated polyester fiber woven fabrics after 5 washings according to JIS L1091 (1999) and after 5 dry cleanings according to JIS L1018 (1999). For the evaluation, the afterflame time and the number of times contacted with the flame were recorded 3 times in accordance with JIS. The results are summarized in Table 1.

TABLE 1

| Flame retardant treating agent | treatment method | Flameproof performance test | | | | | |
|---|---|---|---|---|---|---|---|
| | | Afterflame time (sec) | | | Times contacted with flame | | |
| | | No washing | After 5 washings | After 5 dry cleanings | No washing | After 5 washings | After 5 dry cleanings |
| Example 1 | A | 0,0,0 | 0,0,0 | 0,0,0 | 5,4,4 | 5,4,4 | 5,4,4 |
| Example 2 | A | 0,0,0 | 0,0,0 | 0,0,0 | 5,5,4 | 5,5,4 | 5,5,4 |
| Example 3 | A | 0,0,0 | 0,0,0 | 0,0,0 | 5,5,4 | 5,5,4 | 5,5,4 |
| Example 4 | A | 0,0,0 | 0,0,0 | 0,0,0 | 5,5,5 | 5,5,4 | 5,5,4 |
| Example 5 | A | 0,0,0 | 0,0,0 | 0,0,0 | 5,5,4 | 5,4,4 | 5,5,4 |
| Example 6 | A | 0,0,0 | 0,0,0 | 0,0,0 | 5,5,4 | 5,5,4 | 5,5,4 |
| Comp. Ex. 1 | A | 0,0,0 | 0,0,0 | 0,0,0 | 4,4,4 | 4,4,4 | 4,4,4 |
| Example 1 | B | 0,0,0 | 0,0,0 | 0,0,0 | 5,5,4 | 5,5,4 | 5,5,4 |
| Example 2 | B | 0,0,0 | 0,0,0 | 0,0,0 | 5,5,5 | 5,5,4 | 5,5,4 |
| Example 3 | B | 0,0,0 | 0,0,0 | 0,0,0 | 5,5,4 | 5,5,4 | 5,5,4 |
| Example 4 | B | 0,0,0 | 0,0,0 | 0,0,0 | 5,5,4 | 5,5,4 | 5,5,4 |
| Example 5 | B | 0,0,0 | 0,0,0 | 0,0,0 | 5,5,4 | 5,5,4 | 5,5,5 |
| Example 6 | B | 0,0,0 | 0,0,0 | 0,0,0 | 5,5,4 | 5,5,4 | 5,5,4 |
| Comp. Ex. 1 | B | 0,0,0 | 0,0,0 | 0,0,0 | 5,4,4 | 5,4,4 | 5,4,4 |
| Example 1 | C | 0,0,0 | 0,0,0 | 0,0,0 | 5,5,4 | 5,5,4 | 5,5,4 |
| Example 2 | C | 0,0,0 | 0,0,0 | 0,0,0 | 5,5,5 | 5,5,4 | 5,5,4 |
| Example 3 | C | 0,0,0 | 0,0,0 | 0,0,0 | 5,5,4 | 5,5,4 | 5,5,4 |
| Example 4 | C | 0,0,0 | 0,0,0 | 0,0,0 | 5,5,5 | 5,5,4 | 5,5,4 |
| Example 5 | C | 0,0,0 | 0,0,0 | 0,0,0 | 5,5,5 | 5,5,4 | 5,5,4 |
| Example 6 | C | 0,0,0 | 0,0,0 | 0,0,0 | 5,5,4 | 5,5,4 | 5,5,4 |
| Comp. Ex. 1 | C | 0,0,0 | 0,0,0 | 0,0,0 | 5,4,4 | 5,4,4 | 5,4,4 |
| Untreated | — | 50 | 52 | 50 | 1,1,1 | 1,1,1 | 1,1,1 |

The results in Table 1 demonstrate that the polyester fiber woven fabrics subjected to a flame retardant treating process of the invention all exhibited a flame retardant property which was equivalent or superior compared to the conventional hexabromocyclododecane flame retardant treating agent, regardless of the treatment method employed, and this effect was maintained even after water washing and dry cleaning. Thus, flame retardant treating using flame retardant treating agents according to the invention can impart a highly washing-durable and dry cleaning-durable flame retardant property to fibers. Furthermore, since the flame retardant treating agents of the invention do not employ halogen compounds as flame retarding components, they generate no harmful halogen gases or residues during combustion even when the flame retardant treated fiber products are burned, for example, and they are therefore highly preferred from the standpoint of environmental conservation.

Example 7

(1) The Following Thermoplastic Polymers were Used for Flame Retardant Treatment.
Polybutylene terephthalate (hereinafter, "PBT")
Nylon-6 (hereinafter, "N-6")
Nylon-6,6 (hereinafter, "N-6,6")

(2) The Following Components A and B were Used as Flame Retardant Treating Agents.
Component A: Phosphorus-based compound represented by formula (4).
Component B: Melamine cyanurate (hereinafter, "MC"), melamine phosphate (hereinafter, "MP") and melamine polyphosphate (hereinafter, "MPP").

(3) Production and Treatment of Flame Retardant Plastic Molding Materials
Pellets of each of the thermoplastic polymers listed in (1) above and the flame retardant treating agent comprising component A and component B in (2) above were combined in the prescribed content ratios, and the mixture was blended to uniformity with a twin-screw extruder (Leistritz LSM 30/34 type) at a temperature of 240–280° C. (for PBT and N-6) or 260–300° C. (for N-6,6). The uniform polymer extrusion was drawn out and cooled in a water bath to make pellets.

The pellets were thoroughly dried to obtain plastic molding materials which were then subjected to molding working using an injection molding machine (Model IS 100 EN by Toshiba) at a melt temperature of 260–280° C. (for PBT and N-6) or 270–300° C. (for N-6,6), in order to fabricate flame retardant plastic molding material test samples.

Example 8

Flame retardant plastic molding material test samples were fabricated in the same manner as Example 7, except that glass fiber-reinforced PBT, N-6 and N-6,6 were used as the thermoplastic polymers and MPP-containing components A and B were used as the flame retardant treating agent, in the prescribed content ratios.

Comparative Example 2

Flame retardant plastic molding material test samples were fabricated in the same manner as Example 7, except that glass fiber-reinforced PBT, N-6 and N-6,6 were used as the thermoplastic polymers and each of the components B (MC, MP, MPP) were used with aluminum diphenylphosphinate as the flame retardant treating agent, in the prescribed content ratios.

(Flame Retardant Property Test 2 and Workability Evaluation Test)
The test pieces obtained in Examples 7 and 8 and Comparative Example 2 were supplied for a UL94 test (Underwriters Laboratories), to evaluate the flame retardant properties and assign a "rating" to each according to the test standard. The results are shown in Table 2. The notation "n.c." in the table indicates that no rating was possible. The "1.6 mm" in the rating column indicates the test sample length.

TABLE 2

| | Thermoplastic polymer | | Proportion used with respect to polymer (wt %) | | | | UL94 rating (1.6 mm) |
|---|---|---|---|---|---|---|---|
| | | Glass fiber-reinforcement | | | Component B | | |
| | Type | | Component A | MC | MP | MPP | |
| Example 7 | PBT | no | 10 | 10 | — | — | V-0 |
| | | | 10 | — | 10 | — | V-0 |
| | | | 10 | — | — | 10 | V-0 |
| | | | 10 | 5 | — | — | V-0 |
| | N-6 | | 10 | — | 5 | — | V-0 |
| | | | 10 | — | — | 5 | V-0 |
| | | | 10 | 5 | — | — | V-1 |
| | N-6, 6 | | 10 | — | 5 | — | V-1 |
| | | | 10 | — | — | 5 | V-1 |
| Example 8 | PBT | yes | 10 | — | — | 10 | V-0 |
| | N-6 | | 10 | — | — | 5 | V-0 |
| | N-6, 6 | | 8 | — | — | 4 | V-1 |
| | N-6, 6 | | 10 | — | — | 5 | V-1 |
| Comp. Ex. 2 | PBT | yes | 20 | — | — | 20 | V-1 |
| | N-6 | | 20 | — | — | 20 | V-2 |
| | N-6, 6 | | 20 | — | — | 20 | V-2 |

As explained above, the flame retardant treating agents of the invention and the flame retardant treating process employing them, as well as flame retardant treated articles treated therewith, are able to impart adequate flame retardance to polymer materials such as fibers and thermoplastic polymers even when used in small amounts, while adequate cleaning durability can be contained while containing no halogen compounds.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A flame retardant treating agent which comprises a phosphorus-based compound represented by the following formula (1) and/or its salt:

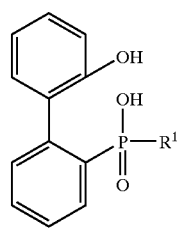

(1)

wherein R¹ represents a hydroxyalkyl, or a substituted or unsubstituted aralkyl group, or a group represented by the following formula (2):

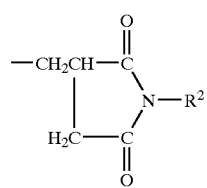

(2)

wherein R² represents an alkyl group of 1–10 carbons.

2. A flame retardant treating agent according to claim 1, by further comprising at least one type of melamine-based compound, comprising a melamine condensation product, the reaction product of melamine and phosphoric acid, or the reaction product of a melamine condensation product and phosphoric acid.

3. A flame retardant treating agent according to claim 1, wherein said phosphorus-based compound comprises an alkali metal salt, alkaline earth metal salt, aluminum salt, zinc salt, ammonium salt or alkanolamine salt of 2–9 carbons.

4. A flame retardant treating process comprising a flame retardant treating agent providing step wherein fiber is treated with a flame retardant treating agent according to claim 1, and a heat treatment step wherein said fiber treated with said flame retardant treating agent is subjected to heat.

5. A flame retardant treating process according to claim 4, wherein in said heat treatment step, said fiber is heat treated at a temperature in the range of 100–220° C. to fix said flame retardant treating agent to said fiber.

6. A flame retardant treating process according to claim 4, wherein in said flame retardant treating agent providing step, said fiber is immersed in a treatment solution containing said flame retardant treating agent to treat said fiber with said flame retardant treating agent, and in said heat treatment step, said treatment solution is heated to a temperature in the range of 90–150° C. to fix said flame retardant treating agent to said fiber.

7. A flame retardant treating process according to claim 4, wherein in said flame retardant treating agent providing step, said fiber is immersed in a treatment solution containing said flame retardant treating agent and a carrier to treat said fiber with said flame retardant treating agent, and in said heat treatment step, said treatment solution is heated to a temperature in the range of 80–130° C. to fix said flame retardant treating agent to said fiber.

8. A flame retardant treating process comprising a flame retardant treating agent providing step wherein a thermoplastic polymer is treated with a flame retardant treating agent according to claim 1.

9. A flame retardant treating process according to claim 8, wherein in said flame retardant treating agent providing step, the thermoplastic polymer comprises HIPS (high-impact polystyrene), polyphenylene ether, polyamide, polyester, polyethylene, polypropylene, polycarbonate, ABS (acrylonitrile-butadiene-styrene), PC/ABS (polycarbonate/acrylonitrile-butadiene-styrene) blend or PPE/HIPS (polyphenylene ether/high-impact polystyrene) blend.

10. A flame retardant treating process according to claim 8, wherein in said flame retardant treating agent providing step, said phosphorus-based compound and/or its salt is used in a concentration range of 1–30 wt % with respect to said thermoplastic polymer, and a melamine-based compound is used in a concentration range of 1–30 wt % with respect to said thermoplastic polymer.

11. A flame retardant treated article comprising fiber having fixed therein a phosphorus-based compound represented by formula (1) and/or a salt of said phosphorus-based compound:

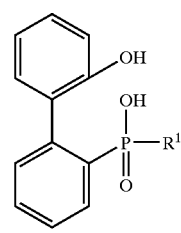

(1)

wherein R¹ represents a hydroxyalkyl, or a substituted or unsubstituted aralkyl group, or a group represented by the following formula (2):

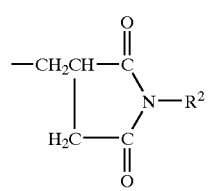

(2)

wherein R² represents an alkyl group of 1–10 carbons.

12. A flame retardant treated article comprising a thermoplastic polymer having fixed therein or containing a phosphorus-based compound represented by formula (1) and/or a salt of said phosphorus-based compound:

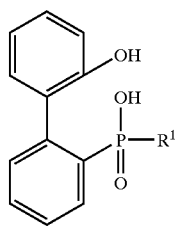

(1)

wherein R¹ represents a hydroxyalkyl, or a substituted or unsubstituted aralkyl group, or a group represented by the following formula (2):

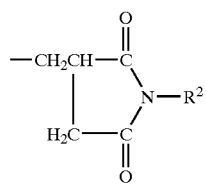

(2)

wherein $R^2$ represents an alkyl group of 1–10 carbons, or a phosphorus-based compound and/or a salt of said phosphorus-based compound with at least one type of melamine-based compound comprising a melamine condensation product, the reaction product of melamine and phosphoric acid, or the reaction product of a melamine condensation product and phosphoric acid.

13. A flame retardant treated article according to claim 11, wherein said salt of said phosphorus-based compound is an alkali metal salt, alkaline earth metal salt, aluminum salt, zinc salt, ammonium salt, or amine salt.

14. A flame retardant treated article according to claim 12, wherein said salt of said phosphorus-based compound is an alkali metal salt, alkaline earth metal salt, aluminum salt, zinc salt, ammonium salt, or amine salt.

* * * * *